(12) United States Patent  (10) Patent No.: US 6,190,310 B1
Cook                      (45) Date of Patent:    Feb. 20, 2001

(54) DISPOSABLE OTOSCOPE TIP SYSTEM

(75) Inventor: Daniel G. Cook, Maple Plain, MN (US)

(73) Assignee: Health & Technology, Inc., Edina, MN (US)

( * ) Notice: Under 35 U.S.C. 154(b), the term of this patent shall be extended for 0 days.

(21) Appl. No.: 09/320,342

(22) Filed: May 26, 1999

(51) Int. Cl.[7] ....................................................... A61B 1/22
(52) U.S. Cl. ................................................................ 600/200
(58) Field of Search .................................. 600/200, 194, 600/199, 193, 196, 197

(56) References Cited

U.S. PATENT DOCUMENTS

| | | | |
|---|---|---|---|
| 672,317 | * | 4/1901 | Dow ...................................... 600/200 |
| 1,346,200 | * | 7/1920 | Harris ................................... 600/200 |
| 1,618,900 | * | 3/1927 | De Zeng ............................... 600/200 |
| 1,686,041 | * | 10/1928 | Smith ................................... 600/200 |
| 1,934,698 | * | 11/1933 | Cameron .............................. 600/200 |
| 2,435,400 | * | 2/1948 | Long ..................................... 600/193 |
| 2,678,041 | * | 5/1954 | Thorburn et al. ..................... 600/197 |
| 3,146,775 | * | 9/1964 | Moore et al. ......................... 600/200 |
| 3,698,387 | * | 10/1972 | Moor et al. ........................... 600/200 |
| 3,878,836 | * | 4/1975 | Twentier .............................. 600/200 |
| 3,934,578 | * | 1/1976 | Heine ................................... 600/200 |
| 4,366,811 | * | 1/1983 | Riester ................................. 600/200 |
| 4,380,998 | * | 4/1983 | Kieffer, II et al. ................... 600/200 |
| 4,643,171 | * | 2/1987 | Riester ................................. 600/200 |
| 5,038,755 | * | 8/1991 | Burgio .................................. 600/200 |

\* cited by examiner

Primary Examiner—Paul J. Hirsch
(74) Attorney, Agent, or Firm—Kinney & Lange, P.A.

(57) ABSTRACT

A disposable otoscope tip system that mounts to a head of an otoscope. The system comprising a receptacle that mounts to the head of the otoscope and a conical member that is secured to the receptacle. The conical member having a first and a second open end. The first open end includes a lip and has a greater diameter than the second open end. The first open end of the conical member being connected to the receptacle by a shoulder which extends radially inward from an inner surface of a neck to secure the lip therein.

39 Claims, 5 Drawing Sheets

DISPOSABLE OTOSCOPE TIP SYSTEM

BACKGROUND OF THE INVENTION

The present invention pertains to an otoscope tip. More particularly, the invention pertains to a disposable otoscope tip system.

Otoscopes are used by medical personnel primarily for examination of external auditory canals and less frequently for examining nasal passages. A standard otoscope includes a handle, a shaft and a head. The shaft extends from the handle, and the head is secured on top of the shaft. The handle is generally made of stainless steel, while the head and shaft may be made from either stainless steel or formed hard plastic. The stainless steel handle typically is silver in color, while the color of the shaft and head will vary depending upon the type of material from which each is made. If the shaft or head are made of stainless steel, then they will also be silver in color. If they are made of formed hard plastic, then they are generally black in color.

The head of a standard otoscope includes a magnifying lens and a light to enlarge and illuminate a targeted area for examination. The head may also include a port which is connected to an inner lumen having an outlet within an annular opening that is across a front of the otoscope head. A disposable tip having a conical shape is attached across the annular opening at the front of the head of the otoscope to direct the field of view onto the small targeted area. The conical shape of the disposable tip facilitates examination of the external auditory canal or nasal passage. If the head of the otoscope includes a port, then air is typically blown through the lumen, out of the outlet, into the disposable tip and across the targeted area to observe movement of hair filaments.

There are primarily two types of otoscopes used which represent approximately eighty percent of all otoscopes. The first type is a diagnostic or notch style otoscope, and the second type is a pneumatic or friction style otoscope. The significant difference between the two types of otoscopes is the manner in which the disposable tip is attached to the head of the otoscope.

The disposable tip in the diagnostic or notch style of otoscope is attached to the head of the otoscope by a key-way system. The head generally includes a key-way, or notch, around the surface defining the annular opening that receives the disposable tip. Likewise, the disposable tip has a key, or a radial outward extension formed along its outer surface to mate with the key-way on the surface defining the annular opening at the head of the otoscope. The disposable tip is then twisted into the annular opening of the otoscope head. Once the disposable tip is secured to the head of the otoscope, the otoscope can be used to view into the ear or nose of a patient during a medical examination.

The smaller end of the conical disposable tip defines the targeted area, or field of view. The smaller sized end of the disposable tip typically has one of two different size diameters, 2.5 millimeters and 4.0 millimeters. The size of the diameter that is used depends upon the size of the canal or passage being examined, which is generally related to the age of the individual being examined. Babies and young children generally require use of the smaller 2.5 millimeter diameter tip, while the larger 4.0 millimeter diameter tip can be used with older children and adults.

The disposable tip, however, does not always stay attached to the head of the notched style otoscope. The disposable tip may become unattached if the key on the disposable tip was not mated correctly with the key-way on the surface defining the annular opening of the otoscope head when it was secured. Additionally, during the examination, the disposable tip may be twisted or turned causing the disposable tip to fall off of the head of the otoscope.

The second style of otoscope, the pneumatic or friction style, attaches the disposable tip to the head of the otoscope by friction. The disposable tip is held onto the surface defining the annular opening of the head of the otoscope by contact between the two surfaces. Movement of the otoscope during the examination tends to loosen this connection. Also, a loose connection may result from the disposable tip not having been sufficiently secured or pushed onto the surface defining the annular opening. Both situations can result in the disposable tip falling off of the head of the otoscope during the examination. The friction style attachment between the disposable tip and the annular opening of the head of the otoscope thus does not provide a very secure means of connection. The disposable tip used with the pneumatic or friction style of otoscope also typically includes openings having either a diameter of 2.5 millimeters or 4.0 millimeters at its smaller diameter end.

Medical personnel within the same facility may use both the notch and the friction style of otoscope. Medical facilities are then forced to stock both types of disposable tips. Because each type of disposable tip has a smaller and a larger opening to define the viewing area, the medical facility is required to maintain and stock at least four different types of disposable tips.

Another problem arises in attempting to use either of the two standard types of otoscopes when examining a young child. The standard otoscopes are uninviting and intimidating to a young child. A young child is unfamiliar with and typically frightened by the otoscope. Young children will typically resist allowing medical personnel to examine them with the otoscope. This usually results in the child's parent or other medical personnel restraining the child in order to conduct the examination. The child's fear and the difficulty of restraining them is only exacerbated when a child has an ailment, such as when they may have an ear infection. The child's sensitivity in the area to be examined, such as the ear, only heightens their uneasiness and fear of the foreign otoscope instrument.

There is no known otoscope disposable tip system which is inviting to children and standardizes a positive and secure connection between a disposable tip and an otoscope.

SUMMARY OF THE INVENTION

The invention is a device and method for a disposable otoscope tip system that is inviting to children and standardizes a positive secure connection between a disposable otoscope tip and an otoscope. The disposable otoscope tip system comprises a hollow conical member and a receptacle. The hollow conical member has a first and a second open end, while the receptacle has an annular passage from a first annular opening to a second annular opening. The first annular opening of the receptacle has securing means which mount the receptacle to a head of the otoscope. The second annular opening of the receptacle has a neck around the annular passage. The neck has a diameter which is slightly larger than the second annular opening of the receptacle. The neck also includes a shoulder around an inner surface of the neck. The first open end of the conical member has a diameter which is larger than a diameter of the second open end of the conical member, but which is slightly less than the diameter of the inner surface of the neck of the receptacle.

The first open end of the conical member also includes a lip that extends radially outward. The lip has an outer diameter which is sized to fit within the neck of the receptacle and which when inserted is secured therein by the shoulder. The first open end of the conical member is thus connected to the neck at the second annular opening of the receptacle.

DETAILED DESCRIPTION

Figure 1:
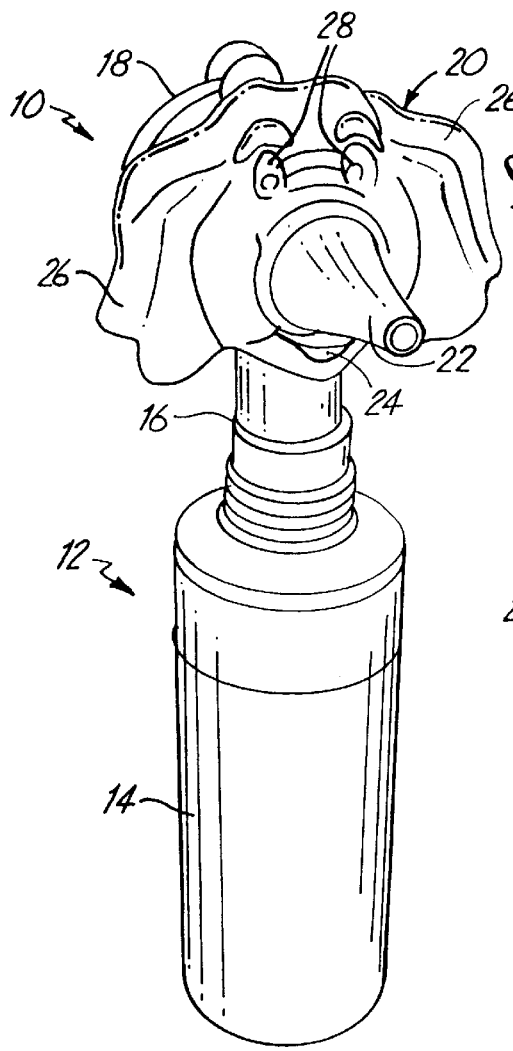
FIG. 1 is a perspective view of a preferred embodiment of the invention.

A preferred embodiment of an otoscope tip system 10 is shown in FIG. 1. The tip system 10 is used in conjunction with an otoscope 12 by medical personnel to examine primarily the external auditory canal of an ear, or less frequently to examine a nasal passage. The otoscope 12 includes a handle 14 from which a shaft 16 extends to a head 18. The tip system 10 is mounted to the head 18 of the otoscope 12. The head 18 includes a lighted magnifying glass to look through for examining a desired area with an enlarged, illuminated view. The head 18 can also include a port which is connected to an interior lumen through the head that terminates in an outlet near the magnifying lens. The port is typically connected to a tube to provide air flow that is directed through the otoscope tip and across the area of observation to view movement of hair filaments as part of the examination. The head 18 and the shaft 16 can be made from either stainless steel or hard formed plastic. If they are made out of stainless steel, then they are generally silver in color. If they are made out of hard formed plastic, then they are generally black in color. The handle 14 is generally made out of stainless steel and is silver in color.

The tip system 10 preferably includes a receptacle 20 and a conical member 22. The receptacle 20 mounts to the head 18 of the otoscope 12. The conical member 22 is secured to the receptacle 20 and defines a small directed field of view through the magnifying lens in the head 18 of the otoscope 12. In a preferred embodiment, the receptacle 20 is formed with facial features of an animal to include a mouth 24, a pair of ears 26, a pair of eyes 28 and a nose that is provided by the conical member 22 when it is secured to the receptacle 20. The facial features incorporated into the receptacle 20, as shown in FIG. 1, are preferably that of an elephant. However, facial features of another animal could be used as well.

Figure 2:
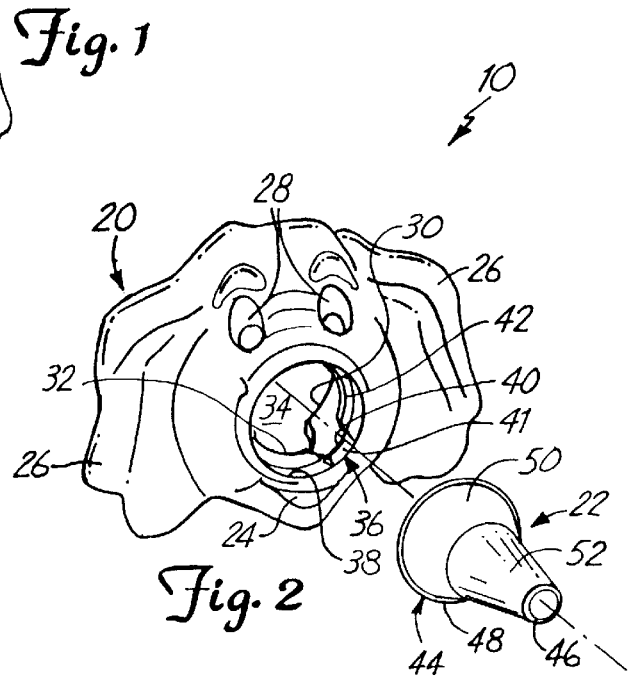
FIG. 2 is an exploded perspective view of the preferred embodiment of the invention.

FIG. 2 is an exploded perspective view of a first embodiment of the disposable otoscope tip system 10. In FIG. 2, the conical member 22 is separated from the receptacle 20. The receptacle 20 includes a first annular opening 30 (at a back side of the receptacle 20 that is only partially shown in FIG. 2), a second annular opening 32 (at a front side of the receptacle 20), and an annular passage 34 therethrough. The second annular opening 32 of the annular passage 34 includes a neck 36 having an inner surface 38. Around the inner surface 38 of the neck 36 is a shoulder 40 which extends radially inward and includes a ramp surface 41 on a side of the shoulder 40 opposite the second annular opening 32. In a preferred embodiment, the shoulder 40 is placed at intermittent locations around the inner surface 38 of the neck 36, rather than being formed continuously around the neck 36.

The second annular opening 32 of the receptacle 20 has a diameter which is less than a diameter of the first annular opening 30. The diameter of the second annular opening 32 is also less than a diameter of the neck 36, which is defined by the inner surface 38. The second annular opening 32 thus creates a radial side wall 42 between the annular passage 34 at the second annular opening 32 and the inner surface 38 of the neck 36. The second annular opening 32 preferably has intermittent breaks that are aligned with the intermittent placement of the shoulder 40 along the inner surface 38 of the neck 36 for ease of manufacturing.

The conical member 22 comprises a first end 44 and a second end 46. The conical member 22 is hollow and has a diameter at the first open end 44 which is larger than a diameter at the second open end 46. A lip 48 preferably extends radially outward from the first end 44 of the conical member 22. The outer diameter of the lip 48 is sized to fit within the neck 36 located at the second annular opening 32 of the receptacle 20, yet be secured by the shoulder 40. In a preferred embodiment, the outer diameter of the lip 48 is approximately 14.8 millimeters, with the lip 48 extending radially outward from the outer surface of the conical member 22 approximately 0.38 millimeters. The diameter of the inner surface 38 defining the neck 36 is therefore slightly larger than 14.8 millimeters (e.g., approximately 15.0 millimeters) to allow the lip 48 to fit therein. The radial side wall 42 preferably extends inward to act as a stop for the first end 44 and defines the second annular opening 32. The second annular opening 32 preferably has an inner diameter of approximately 12.9 millimeters. The shoulder 40 preferably extends radially inward approximately 0.60 millimeters from the inside surface 38 of the neck 36 to secure the lip 48. The conical member 22 and the receptacle 20 are preferably made of formed non-latex, polymeric material, however, substitute materials could also be used.

In a preferred embodiment, the conical member 22 includes a base section 50 and a nozzle section 52. The base section 50 preferably has a greater conical slope than the nozzle section 52. The slope of the base section 50 creates a natural transition from the receptacle 20 when the conical member 22 is attached to the receptacle 20. The slope of the nozzle section 52 directs the field of view onto the small targeted area and assists in the directioning of light from the head 18 of the otoscope 12.

The conical member 22 is secured to the receptacle 20 by applying a compressive force therebetween. The first end 44 of the conical member 22 is inserted into the neck 36 of the receptacle 20. The first end 44 then contacts the ramp surface 41 of the shoulder 40. The conical member 22 is compressed against the ramp surface 41 until it passes over the ramp surface 41 and is stopped by the radial side wall 42. Again, the side wall 42 defines the second annular opening 32 of the annular passage 34 for the receptacle 20 connected to the head 18 of the otoscope 12. At this point, the lip 48, at the first end 44 of the conical member 22, is secured by the shoulder 40 within the neck 36 at the second annular opening 32 of the receptacle 20. As the lip 48 slides over the ramp surface 41 and beyond the shoulder 40, an audible sound or snap generally occurs indicating a positive connection has been made between the conical member 22 and the receptacle 20.

Figure 3A:
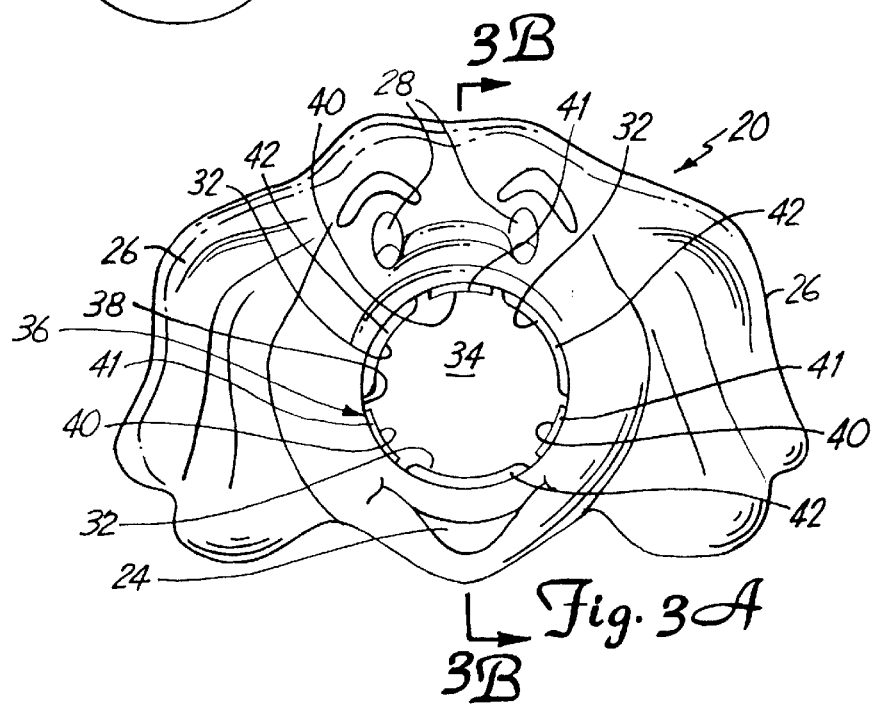
FIG. 3A is a front view of a first embodiment a receptacle.

FIG. 3A is a front view of a first embodiment of the receptacle 20 used with the disposable otoscope tip system 10. FIG. 3A more clearly shows the shoulder 40 and the ramping surface 41 which extend from the inner surface 38 of the neck 36 at the second annular opening 32 of the receptacle 20. The shoulder 40 and the ramping surface 41 extend radially inward from the inner surface 38. In this embodiment of the invention, there are three of the shoulders 40 and the ramping surfaces 41 which extend inward from the inner surface 38 of the neck 36 to retain the lip 48 of the conical member 22. The three shoulders 40 and the three ramping surfaces 41 of the first embodiment of the invention are placed approximately equidistant around the inner surface 38.

Opposite the three shoulders 40 that are within the neck 36, are three sections of the side wall 42 which extend radially inward to define the second annular opening 32 next to a base of the neck 36. The inner diameter of the side wall 42 defines the annular passage 34 at the second annular opening 32 of the receptacle 20. Due to the shorter inner diameter of the side wall 42 compared to the neck 36, the side wall 42 acts as a stop for the conical member 22 when it is compressed into the neck 36 of the receptacle 20. The side wall 42 prevents the first end 44 of the conical member 22 from being compressed beyond the neck 36 of the receptacle 20. As previously discussed, the side wall 42 is preferably placed intermittently around the second annular opening 32 opposite the shoulder 40 for simplified manufacturing purposes. Alternatively, the side wall 42 and the shoulder 40 could each be formed from a continuous ring.

Figure 3B:
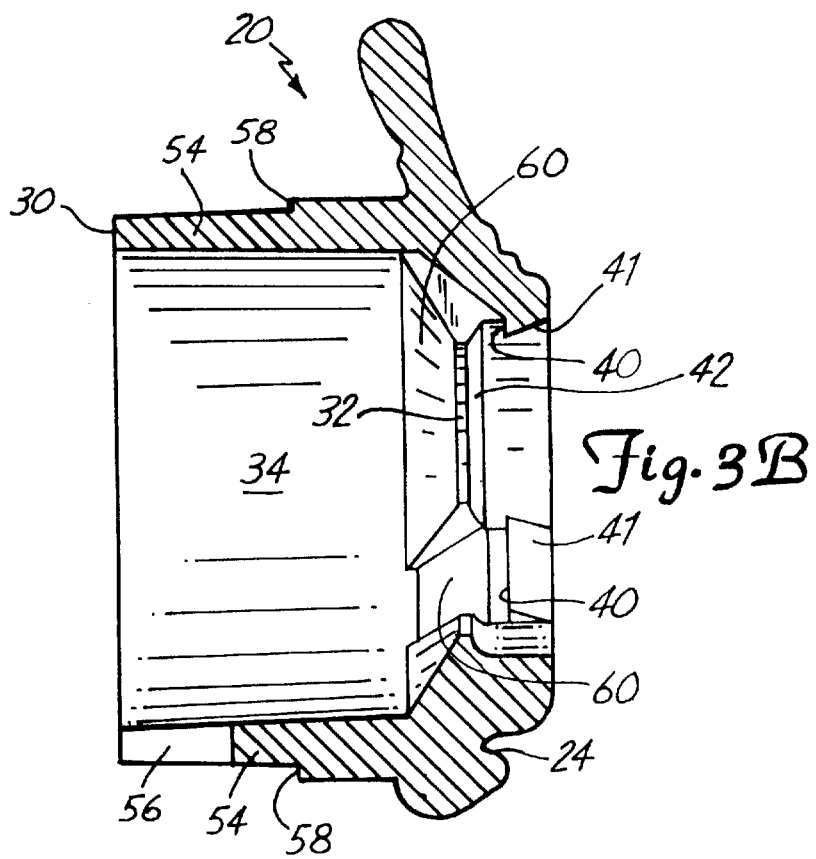
FIG. 3B is a sectional view along section 3B—3B of FIG. 3A.

FIG. 3B is a sectional view along a section 3B—3B of FIG. 3A. FIG. 3B more clearly illustrates the means by which the receptacle 20 is secured to the head 18 of the otoscope 12 in the first embodiment. One of the primary techniques used to secure a standard tip to the head 18 of the otoscope 12 is by friction. For a friction type of otoscope, the first embodiment of the receptacle 20 is used as part of the disposable otoscope tip system 10.

As illustrated in FIG. 3B, the annular passage 34 of the receptacle 20 is in part defined by an annular wall 54. The annular wall 54 terminates at the first annular opening 30 of the receptacle 20. A notch 56 is cut out of a portion of the annular wall 54 at the first annular opening 30 to accommodate the shaft 16 of the otoscope 12 as the receptacle 20 is slid over or within the head 18 of the otoscope 12 for connection. The annular wall 54 extends in an annular direction a sufficient distance to ensure that the receptacle 20 is securely mounted to the head 18 of the otoscope 12. Preferably, the annular wall 54 extends approximately 8 millimeters beyond a radial stop surface 58 formed by an outwardly raised surface in the annular wall 54. The raised stop surface 58 contacts an end of an annular housing on the head 18 of the otoscope 12. The annular wall 54 slides within the annular housing on the head 18 of the otoscope 12 until the radial stop 58 contacts the housing. The notch 56 allows the annular wall 54 to slide further within the housing and partially around the shaft 16 to more securely mount the receptacle 20 to the head 18 of the otoscope 12.

A funnel section 60 is located near the second annular opening 32 of the receptacle 20. The funnel section 60 reduces the diameter of the annular passage 34 defined by the annular wall 54 to the diameter of the side wall 42 at the second annular opening 32. Preferably, that portion of the funnel section 60 that coincides with the side wall 42 has a greater slope than that portion of the funnel section 60 that coincides with the shoulder 40 to simplify manufacturing of the receptacle 20. The funnel section 60 preferably has a slope that creates an angle of approximately 60 degrees with a center line of the annular passage 34 along the section that corresponds to the second annular opening 32. Whereas the funnel section 60 preferably has a slope that creates an angle of approximately 45 degrees with the center line of the annular passage 34 along the section that corresponds to the shoulder 40.

Figure 3C:
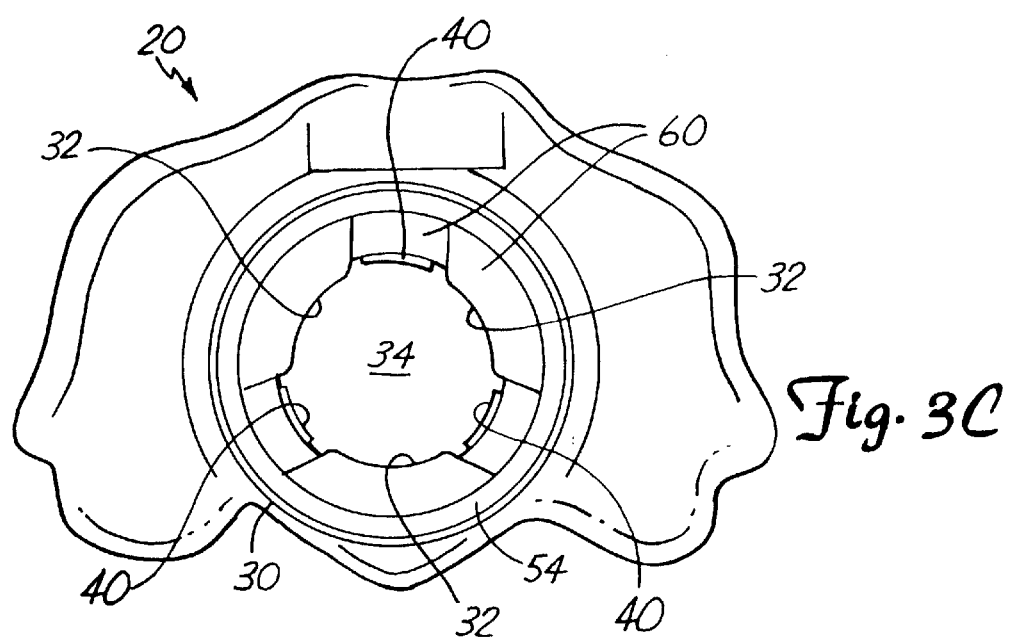
FIG. 3C is a back view of the first embodiment of the receptacle.

FIG. 3C is a back view of a first embodiment of the receptacle 20. The intermittent placement of either the side wall 42 that defines the second annular opening 32 or the shoulder 40 of the receptacle 20 is shown. Additionally, the varying slopes of the funnel section 60 which coincide with the annular opening 32 and the shoulder 40 are also illustrated. As shown in FIG. 3C, the diameter of the annular passage 34 at the second annular opening 32, defined by the side wall 42, is less than the diameter of the first annular opening 30, defined by the annular wall 54.

Figure 4A:
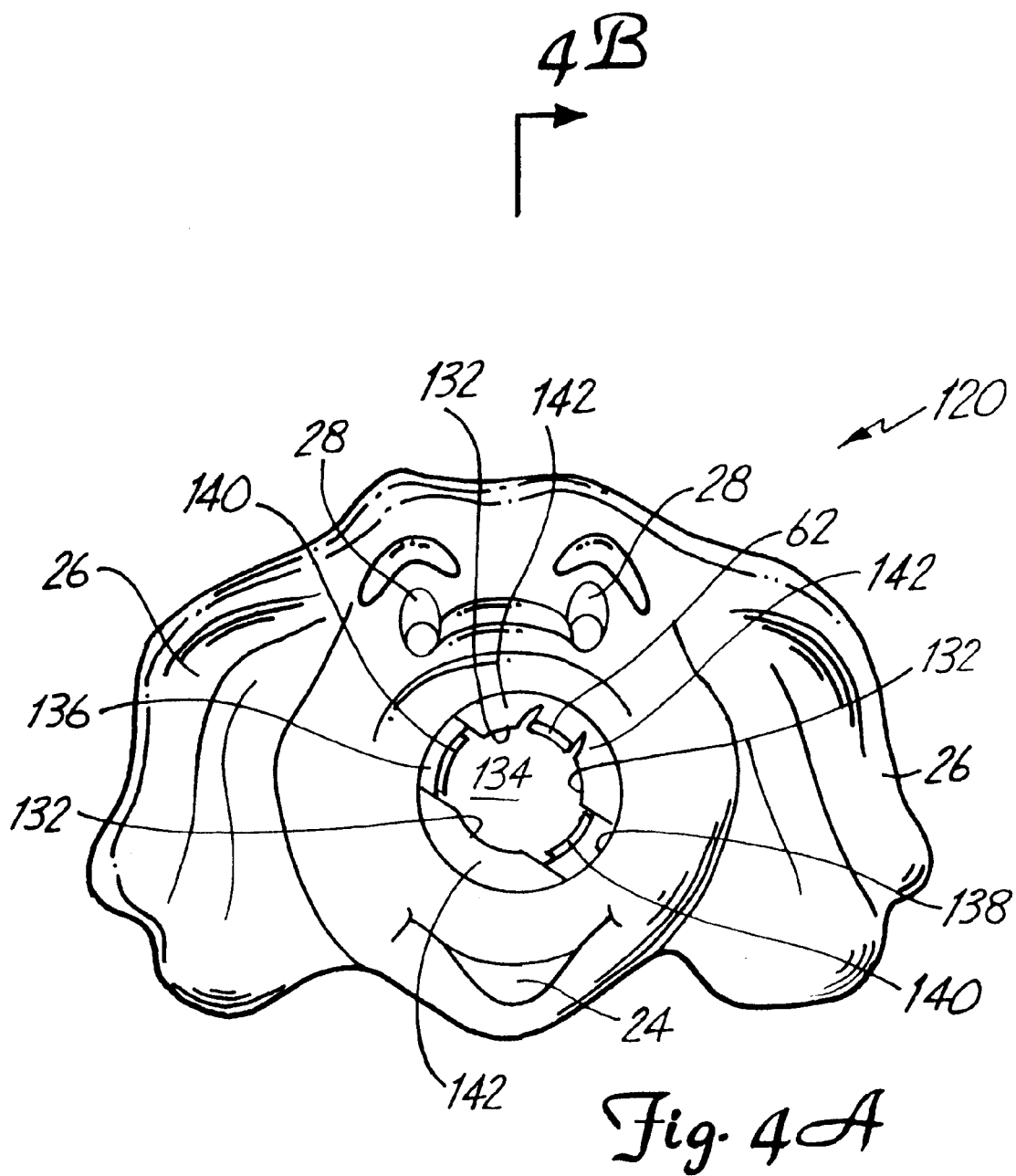
FIG. 4A is a front view of a second embodiment of the receptacle.

FIG. 4A provides a front view of a second embodiment of a receptacle 120 that is used with a notch style of otoscope. The notch style of otoscope utilizes a key-way technique for securing a disposable tip with a key to a housing at a front of a head of the otoscope rather than friction. In order to accommodate this type of mounting technique, a key 62 extends radially inward from within the annular passage 134 to mate with a key-way or groove placed in an annular opening in the head of the notch style of otoscope. By placing the key 62 of the receptacle 120 in the key-way or groove of the head of the notch style of otoscope and twisting, the second embodiment of the receptacle 120 is secured to the head of the otoscope.

Similar to the first embodiment, the second embodiment of the receptacle 120 also includes a shoulder 140 which extends radially inward from an inner surface 138 of a neck 136. The neck 136 is placed at a second annular opening 132 of the receptacle 120. The second annular opening 132 is defined by a side wall 142 which extends radially inward and defines the annular passage 134 at the second annular opening 132. The radial side wall 142 also extends radially inward, further than the shoulders 140, to act as a stop for the first end 44 of the conical member 22. Similar to the first embodiment, the side wall 142 and the shoulder 140 are placed intermittently in an alternating manner around the annular passage 134 for ease of manufacturing. In the second embodiment of the receptacle 120, however, there is no side wall 142 or shoulder 140 placed along that portion of the annular passage 134 that coincides with the key 62. Again, this is done for ease of manufacturing of the receptacle 120.

In a preferred embodiment, the receptacle 120 only includes two of the shoulders 140 to retain the lip 48 of the conical member 22. To ensure a secure connection between the conical member 22 and the receptacle 120, the two shoulders 140 used with the receptacle 120 are placed along the inner surface 138 of the neck 136 opposite each other. The conical member 22 is secured to the receptacle 120 in a manner similar to that used to connect the conical member 22 to the receptacle 20.

Figure 4B:
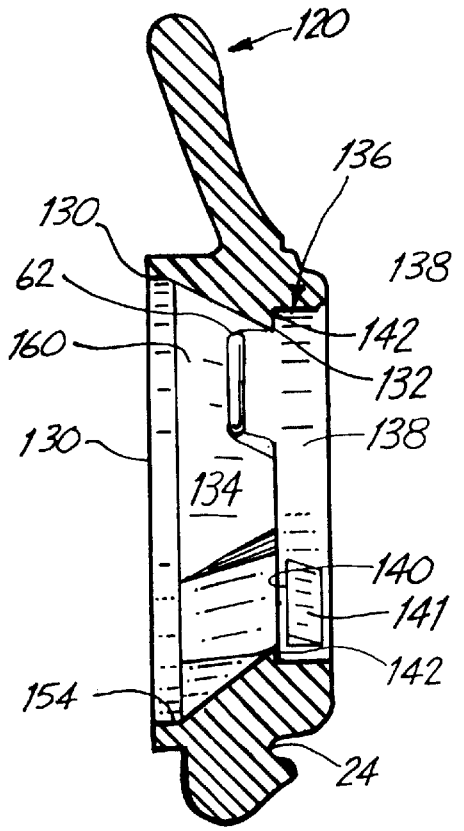
FIG. 4B is a sectional view along section 4B—4B of FIG. 4A.

FIG. 4B is a sectional view along section 4B—4B of FIG. 4A. As illustrated in FIG. 4B, the second embodiment of the receptacle 120 similarly includes an annular wall 154 that defines in part the size of the annular passage 134 and terminates at a first annular opening 130 of the receptacle 120. However, as illustrated in FIG. 4B, the annular wall 154 of the second embodiment is much shorter than the annular wall 54 of the first embodiment. Additionally, the second embodiment of the receptacle 120 also includes a funnel section 160 which reduces a diameter of the annular passage 134 at the second annular opening 132 compared to a diameter defined by the annular wall 154 at the first end 130. Again, the funnel section 160 has a greater slope along that portion which coincides with the side wall 142 and a smaller slope along that portion which coincides with the shoulders 140. The key 62 is preferably placed within the funnel section 160 along a section which coincides with the side walls 142. The side walls 142 preferably contact the housing at the front of the head of the notch style of otoscope. Placing the key 62 in this manner will more likely ensure that the key 62 is maintained within the key-way or groove placed in the head of the notch style of otoscope and more securely mount the receptacle 120.

Figure 4C:
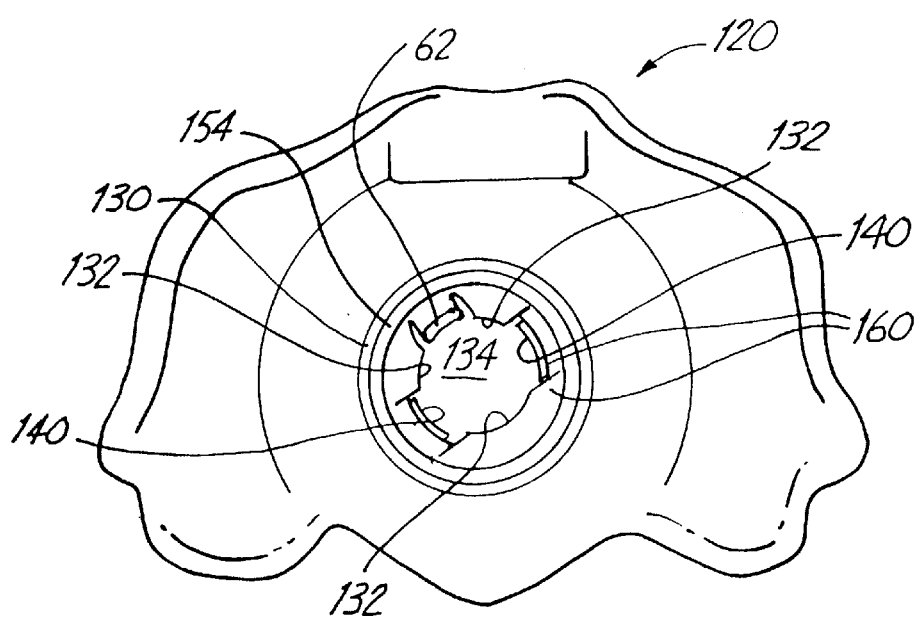
FIG. 4C is a back view of the second embodiment of the receptacle.

FIG. 4C illustrates a back view of the second embodiment of the receptacle 120. As illustrated in FIG. 4C, the diameter of the second annular opening 132 defined by the side wall 142 for the annular passage 134 is less than the diameter defined by the annular wall 154 at the first annular opening 130. Further, the receptacle 120 has two of the shoulders 140 preferably placed opposite each other. Opposite the shoulders 140 are the side walls 142 placed around the second annular opening 132. The funnel section 160 decreases the diameter of the annular passage 134 through the receptacle 120. The funnel section 160 has a steeper slope over that portion which is coincident with the side walls 142, as compared with that portion which coincides with the shoulders 140. The slope of the funnel section 160 that coincides with the key 62 is equal to the slope of the section 160 along the side walls 142. The funnel section 160 creates an angle with a center line of the annular passage 134 of approximately 60 degrees along that section corresponding to the second annular opening 132 and approximately 45 degrees along that section corresponding to the shoulder 140.

Figure 5:
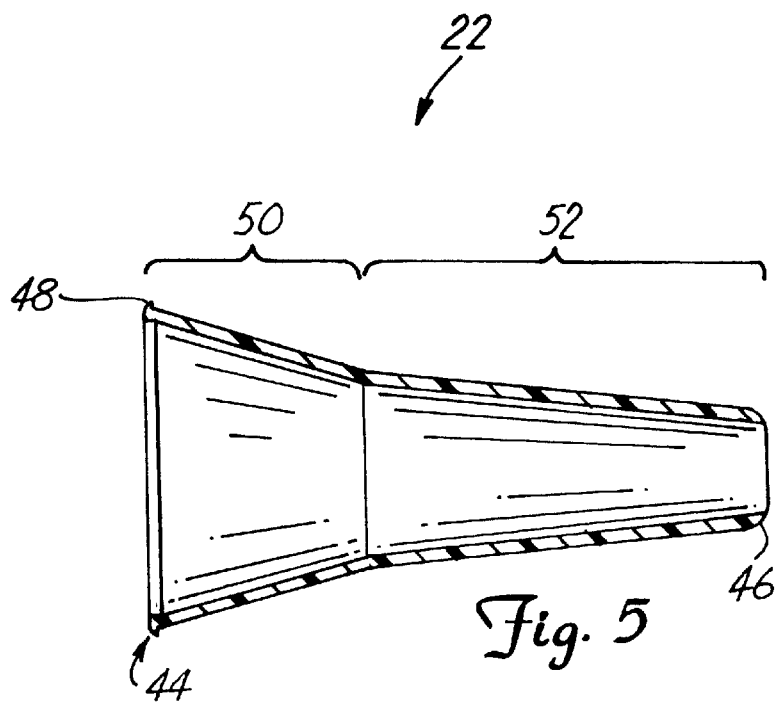
FIG. 5 is a sectional view of a first embodiment of a conical member.

FIG. 5 is a sectional view of the conical member 22. FIG. 5 illustrates the steeper slope of the conical member 22 along the base section 50 as compared with the nozzle section 52. Preferably, the lip 48 at the first end 44 of the conical member 22 extends radially outward, approximately 0.38 millimeters from the outside diameter of the first end 44 of the conical member 22. In a preferred embodiment, the inside diameter of the first end 44 is approximately 13.12 millimeters, and the outer diameter of the lip 48 at the first end 44 is approximately 14.8 millimeters.

The inside diameter at the second end 46 of the conical member 22 is less than the inside diameter at the first end 44. In a preferred embodiment, the inside diameter at the second end 46 can vary to accommodate different situations such as the age of a patient or the size of their external auditory canal. In FIG. 5, the inside diameter of the second end 46 is 4.0 millimeters. The conical member 22 preferably has an overall length of approximately 26.5 millimeters, comprised of the base section 50 having a length of approximately 9.50 millimeters and the nozzle section 52 having a length of approximately 17.0 millimeters.

In a preferred embodiment, the conical member 22 creates an angle of approximately 33.5 degrees along the base section 50 and approximately 12.1 degrees along the nozzle section 52, for the 4.0 millimeter diameter opening at the second end 46. The conical member 22 preferably has a wall thickness of approximately 0.50 millimeters.

Figure 6:
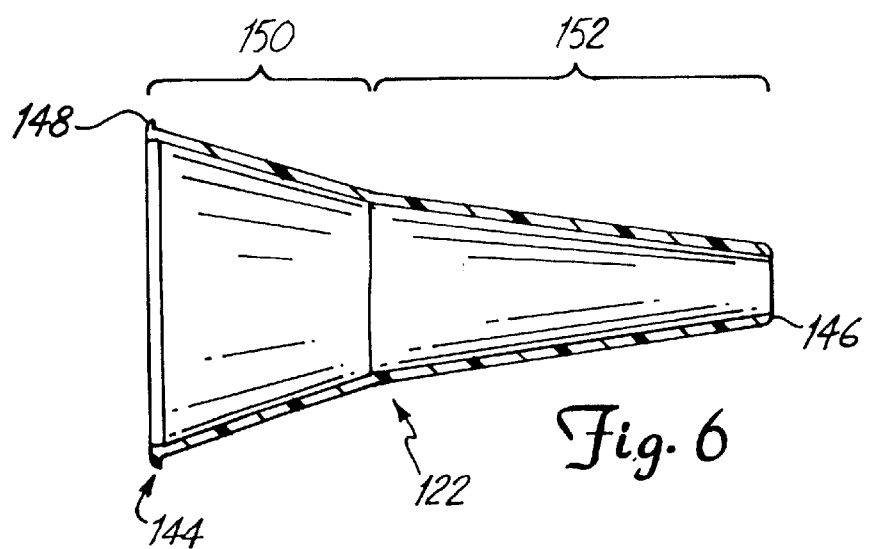
FIG. 6 is a sectional view of a second embodiment of a conical member.

FIG. 6 is a sectional view of a second embodiment of a conical member 122. The second embodiment of the conical member 122 differs from the first embodiment in that the opening at a second end 146 is smaller and thus the slope along a nozzle section 152 is greater. All other dimensions between the two embodiments preferably remain the same.

Similar to the first embodiment, the second embodiment of the conical member 122 has a first end 144 from which a lip 148 extends radially outward. The conical member 122 also includes a base section 150 at the first end 144 and the nozzle section 152 at the second end 146. However, in the second embodiment of the conical member 122, the opening at the second end 146 has a diameter of 2.5 millimeters, instead of 4.0 millimeters. Because all other dimensions are preferably the same between the two embodiments, the smaller diameter opening at the second end 146 causes the nozzle section 152 to have a greater slope angle than the nozzle section 52. The nozzle section 152 has an angle of approximately 16.9 degrees, slightly steeper than the 12.1 degree angle for the nozzle section 52. As a result of all other dimensions remaining the same between the conical members 122 and 22, especially at the first end 144 and 44 respectively, the conical members 122 and 22 are universalized and can be interchangeably used with either of the receptacles 20 or 120. Additionally, either of the conical member 122 or 22 could also be secured directly to an otoscope employing a shoulder type style mounting technique rather than a notch or friction type mounting style.

The disposable otoscope system provides a positive and secure manner of mounting a conical member to a head of an otoscope. The system includes a receptacle which has securing means for connecting to either a notch or a friction style of otoscope, thereby universalizing the type of conical member for the majority of otoscopes used by medical personnel. Universalizing the conical member also benefits medical facilities who will only have to monitor, maintain and deal with stocking one style of conical member, rather than multiple styles. Medical facilities will further benefit from a universalized conical member by being able to buy the same style conical member in greater bulk numbers, thus likely leading to a lower per unit cost.

A further benefit of the disposable otoscope system is that the receptacle and conical member can be formed with facial features of an animal so that when the system is secured to the otoscope it is inviting to children. This will improve the manner and therefore the results of the examination from the perspective of the child, the parents, and the medical personnel performing the examination. The otoscope system is economically constructed from non-latex, polymeric material. The disposable otoscope system is also competitively priced because it, similar to existing tip designs, only requires replacement of the conical member.

Although the present invention has been described with reference to preferred embodiments, workers skilled in the art will recognize that changes may be made in form and detail without departing from the spirit and scope of the invention. For instance, the dimensions of either the receptacle or conical section can be altered. More specifically, the diameter of the second end of the conical member can be adjusted to a desired diameter. Additionally, the side wall defining the annular opening at the second end of the receptacle and the shoulder within the neck of the receptacle can form continuous rings rather than intermittent rings. The conical member can also be formed from a single section defined by a constant angle or a smooth curve. By use of the disposable otoscope tip system, a manner of positively securing a standardized disposable tip to an otoscope that is inviting to children is provided.

What is claimed is:

1. A disposable otoscope tip for use with a receptacle that is mounted on an otoscope, the disposable tip comprising:
   a conical member having a first and a second open end with an open passage therebetween, wherein a diameter of the first open end is greater than a diameter of the second open end; and
   a lip located at the first open end having an outer diameter of approximately 14.8 millimeters that is retained by the receptacle when the conical member is compressed therein and provides the only means for securing the conical member to allow examination through the second open end of the conical member.

2. The disposable otoscope tip of claim 1, wherein the conical member has a wall thickness of approximately 0.50 millimeters.

3. The disposable otoscope tip of claim 1, wherein the lip extends approximately 0.38 millimeters radially outward from the conical member.

4. The disposable otoscope tip of claim 1, wherein the conical member further comprises:
   a base section at the first open end; and
   a nozzle section next to the base section at the second open end,
      wherein the slope of the conical member along the base section is greater than along the nozzle section.

5. The disposable otoscope tip of claim 4, wherein the conical member creates an angle of approximately 33.5 degrees along the base section.

6. The disposable otoscope tip of claim 1 wherein the tip has a length of approximately 26.50 millimeters.

7. The disposable otoscope tip of claim 1, wherein the second open end of the conical member has a diameter of approximately 2.5 millimeters.

8. The disposable otoscope tip of claim 1, wherein the second open end of the conical member has a diameter of approximately 4.0 millimeters.

9. The disposable otoscope tip of claim 1, wherein the conical member along with the receptacle includes facial features of an animal.

10. A disposable otoscope tip system for mounting onto a head of an otoscope, the disposable otoscope tip system comprising:
   a disposable tip which includes a hollow, conical member having a first open end with a diameter that is larger than a diameter of a second open end, a lip that extends radially outward at the first open end of the conical member; and
   a receptacle having an annular passage therethrough from a first annular opening to a second annular opening; the receptacle including:
      a neck around the second annular opening of the receptacle, the neck having a diameter that is slightly larger than the annular passage at the second annular opening of the receptacle to receive within the neck the lip that is located at the first open end of the conical member;
      a shoulder extending radially inward along an inner surface of the neck that retains the lip when the conical member is compressed into the neck and the lip is pushed beyond the shoulder to provide the only means for securing the conical member therein; and
      securing means at the first annular opening of the receptacle for mounting the receptacle to the head of the otoscope.

11. The disposable otoscope tip system of claim 10, wherein the securing means at the first annular opening of the receptacle includes an annular wall for mounting the receptacle to the head of the otoscope by friction.

12. The disposable otoscope tip system of claim 10, wherein the securing means at the first annular opening of the receptacle includes a key which extends radially inward along the annular passage of the receptacle for mounting the receptacle to the head of the otoscope by a key-way system.

13. The disposable otoscope tip system of claim 10, wherein the annular passage at the second annular opening of the receptacle includes a radial side wall at a base of the neck.

14. The disposable otoscope tip system of claim 13, wherein the radial side wall acts as a stop to the first open end of the conical member when it is inserted and secured by the shoulder within the neck of the receptacle.

15. The disposable otoscope tip system of claim 10, wherein the shoulder includes a ramp surface along the inner surface of the neck on a side of the shoulder opposite the second annular opening of the receptacle.

16. The disposable otoscope tip system of claim 10, wherein the lip of the conical member has an outer diameter of approximately 14.8 millimeters.

17. The disposable otoscope tip system of claim 16, wherein the neck has an inner diameter defined by the inner surface of approximately 15.0 millimeters.

18. The disposable otoscope tip system of claim 17, wherein the shoulder extends radially inward approximately 0.60 millimeters from the inner surface of the neck.

19. The disposable otoscope tip system of claim 18, wherein the annular opening at the second end of the receptacle has a diameter of approximately 12.9 millimeters.

20. The disposable otoscope tip system of claim 16, wherein the lip extends radially outward from the conical member approximately 0.38 millimeters.

21. The disposable otoscope tip system of claim 10, wherein the receptacle includes facial features of an animal.

22. A disposable otoscope tip system for mounting onto a head of an otoscope, the disposable tip system comprising:
   a receptacle including:
      a first and a second annular opening;
      a passage along an annular axis of the receptacle from a center of the first annular opening to a center of the second annular opening, the first annular opening having a larger diameter than the second annular opening;
      securing means at the first annular opening for mounting the receptacle to the head of the otoscope;
      a neck located at the second annular opening which has an inner surface with a diameter that is greater than the diameter at the second annular opening; and
      a shoulder along the inner surface of the neck extending radially inward; and
   a disposable tip which includes a hollow, conical member having a first and a second open end, such that a diameter of the first open end fits within the inner surface of the neck and is larger than a diameter of the second annular opening, and a lip that extends radially outward from the first open end of the conical member, and is retained within the neck of the receptacle by the shoulder when the conical member is compressed therein to provide the only means for securing the conical member to the receptacle.

23. The disposable otoscope tip system of claim 22, wherein the securing means at the first annular opening of the receptacle includes an annular wall for mounting the receptacle to the head of the otoscope by friction.

24. The disposable otoscope tip system of claim 22, wherein the securing means at the first annular opening of the receptacle includes a key that extends radially inward from the passage within the receptacle for mounting the receptacle to the head of the otoscope by a key-way system.

25. The disposable otoscope tip system of claim 22, wherein the shoulder includes a ramp surface along the inner surface of the neck on a side of the shoulder opposite the second annular opening of the receptacle.

26. The disposable otoscope tip system of claim 22, wherein the neck has an inner diameter defined by the inner surface of approximately 15.0 millimeters.

27. The disposable otoscope tip system of claim 26, wherein the shoulder extends radially inward approximately 0.60 millimeters from the inner surface of the neck.

28. The disposable otoscope tip system of claim 27, wherein the lip of the conical member has an outer diameter of approximately 14.8 millimeters.

29. The disposable otoscope tip system of claim 28, wherein the lip extends radially outward from the conical member approximately 0.38 millimeters.

30. The disposable otoscope tip system of claim 22, wherein the conical member further comprises:
   a base section at the first open end; and
   a nozzle section next to the base section at the second open end,
      wherein the slope of the conical member along the base section is greater than along the nozzle section.

31. The disposable otoscope tip system of claim 30 wherein the tip has a length of approximately 26.50 millimeters.

32. The disposable otoscope tip system of claim 22, wherein the second open end of the conical member has a diameter of approximately 2.5 millimeters.

33. The disposable otoscope tip system of claim 22, wherein the second open end of the conical member has a diameter of approximately 4.0 millimeters.

34. A method of mounting a disposable otoscope tip onto a receptacle secured to an otoscope, the method including:
   aligning a first open end of a hollow conical member with the receptacle of the otoscope, the receptacle having facial features of an animal; and
   pushing the conical member so that the first open end is received into the receptacle on the otoscope until a lip, which extends radially outward from the first open end of the conical member and has an outer diameter of approximately 14.8 millimeters, is secured by a shoulder, which extends radially inward along an inner surface of a neck in the receptacle, to provide the only means for securing the conical member and completing the facial features created by the receptacle.

35. The method of claim 34 and further including pushing the conical member so that the lip at the first open end is secured by the shoulder and the first open end of the conical member contacts a stop surface at a base of the neck created by a radial side wall which defines an annular passage at a second annular opening of the receptacle, the second annular opening having a diameter that is less than a diameter of the annular passage at a first annular opening of the receptacle which mounts the receptacle to the otoscope.

36. A method of mounting a disposable otoscope tip system comprising:
   attaching a receptacle having some facial features of an animal to an otoscope, the receptacle having an annular passage between a first and a second annular opening, such that the first annular opening is mounted to a head of the otoscope while the second annular opening has a neck with an inner surface from which a shoulder extends radially inward; and
   attaching a first open end of a conical member to the receptacle by compression, wherein the conical member functions as a component in developing the facial features of the animal, the first open end having a greater diameter than a second open end of the conical member and having a lip extending radially outward from the first open end, wherein the lip is retained by the shoulder within the neck of the receptacle when the conical member is compressed therein providing the only means for securing the conical member to the receptacle and to complete the facial features created by the otoscope tip system.

37. The method of claim 36 and further including sliding an annular wall of the receptacle which defines the annular passage at the first annular opening into a housing on a head of the otoscope to attach the receptacle to the otoscope by friction between the annular wall and the housing.

38. The method of claim 36 and further including:
   placing a key that extends radially inward from the annular passage of the receptacle into a key-way on a head of the otoscope; and
   twisting the receptacle relative to the otoscope to cause the key on the receptacle to travel along the key-way of the otoscope to secure the receptacle to the otoscope.

39. The method of claim 36 and further including the receptacle having facial features of an animal.

* * * * *